United States Patent [19]

Shimp et al.

[11] Patent Number: 4,487,948

[45] Date of Patent: Dec. 11, 1984

[54] POLYGLYCIDYL HINDERED AROMATIC AMINES

[75] Inventors: David A. Shimp, Prospect; Richard B. Graver, Louisville, both of Ky.

[73] Assignee: Celanese Corporation, New York, N.Y.

[21] Appl. No.: 477,993

[22] Filed: Mar. 23, 1983

[51] Int. Cl.$^3$ ............................................. C07D 303/36
[52] U.S. Cl. ..................................... 549/552; 528/363; 528/407; 528/418
[58] Field of Search ............................................. 549/552

[56] References Cited

U.S. PATENT DOCUMENTS

| | | | |
|---|---|---|---|
| 2,951,822 | 9/1960 | Reinking | 260/42 |
| 2,951,825 | 9/1960 | Reinking et al. | 260/47 |
| 2,953,579 | 9/1960 | Williams et al. | 549/552 |
| 3,310,528 | 3/1967 | Garnish | 260/47 |
| 3,360,486 | 12/1967 | Garnish | 260/2 |
| 3,798,242 | 3/1974 | Batzer et al. | 549/552 |
| 3,875,190 | 4/1975 | Habermeier et al. | 549/552 |

OTHER PUBLICATIONS

Ciba-Geigy Product Data–Epoxy Resin 0500.
Ciba-Geigy Product Data–Epoxy Resin 0510.
Ciba-Geigy Product Data–Araldite MY720.
Sherwin-Williams Technical Bulletin IPNA-1.

*Primary Examiner*—Norma S. Milestone
*Attorney, Agent, or Firm*—Herbert P. Price

[57] ABSTRACT

Polyglycidyl amines having room temperature latency when blended with curing agents and high heat distortion temperatures when cured are derived from hindered aromatic diamines and epihalohydrins. Cured products obtained from these polyglycidyl amines and curing agents are useful in structural composites, film adhesives, molding compounds and the like.

7 Claims, No Drawings

4,487,948

POLYGLYCIDYL HINDERED AROMATIC AMINES

BACKGROUND OF THE INVENTION

The field of art to which this invention pertains is curable polyepoxides based on the reaction products of epichlorohydrin and aromatic amines, i.e., polyglycidyl aromatic amines.

Polyglycidyl aromatic amines are described in U.S. Pat. No. 2,951,822. The aromatic amines from which the glycidyl compounds are derived are described as being free of non-amino groups reactive with a halohydrin. Examples of such amines are aniline, 2,6-dimethylaniline, p-toluidine, m-chloroaniline, p-amino diphenyl, p-phenylene diamine, 4,4'-diamino diphenyl methane, benzidine, and the like.

Polyglycidyl compounds derived from epihalohydrins and aminophenols are described in U.S. Pat. No. 2,951,825.

Processes for preparing polyglycidyl aromatic amines are described in U.S. Pat. Nos. 3,310,528 and 3,360,486.

Commercially available glycidyl amines are Araldite MY720 and Epoxy Resin 0510, both of which are made by Ciba-Geigy Corporation. Araldite MY720 is N,N,N',N'-tetraglycidyl methylene dianiline. Epoxy Resin 0510 is derived from epichlorohydrin and p-aminophenol. Other polyglycidyl amine epoxy systems are sold by Sherwin-Williams Company, namely, PGA-X, which is N,N,N',N'-tetraglycidyl metaxylylene diamine, and PGA-C, which is N,N,N',N'-tetraglycidyl 1,3-bis(aminomethyl) cyclohexane.

SUMMARY OF THE INVENTION

This invention is directed to polyglycidyl amine compounds. In particular, this invention pertains to polyglycidyl amines wherein the amines are hindered aromatic polyamines.

The compositions of this invention are polyglycidyl amines derived from epihalohydrins and aromatic polyamines. The amines are sterically hindered aromatic diamines containing two primary amine groups attached directly to carbon atoms in the aromatic nucleus wherein the carbon atoms are not adjacent to each other and wherein each position ortho to each amine group contains an alkyl substituent having one to three carbon atoms. The polyglycidyl amines are referred to as tetraglycidyl amines and have epoxide functionalities between 3 and 4.

The polyglycidyl hindered aromatic amines of this invention have improved stability at elevated temperatures over the prior art glycidyl amines based on unhindered amines. They exhibit latency in combination with amine curing agents when stored at room temperature. When cured with epoxy resin curing agents, the cured castings have high heat distortion temperatures, both dry and wet, and low water absorption.

The products of this invention are very versatile, exhibiting a unique combination of handling features and high temperature performance properties. These compositions are useful in structural composites, filament wound pipes, pultruded rods, film adhesives, molding compounds, printed wiring boards and the like.

DESCRIPTION OF THE INVENTION

The hindered aromatic diamines useful in this invention are sterically hindered aromatic diamines containing two primary amine groups. The two primary amine groups are attached directly to non-adjacent carbon atoms in the aromatic nucleus. Each position ortho to each amine group contains an alkyl substituent having one to three carbon atoms. Preferred hindered amines are those wherein no more than one position ortho to each amine group contains a methyl substituent. Particularly preferred hindered amines are those wherein at least 3 of the positions ortho to the amine groups contain $C_2$ or $C_3$ alkyl substituents. These hindered aromatic diamines can be mononuclear or dinuclear. If dinuclear, one primary amine group is attached to each aromatic nucleus. Examples of such hindered aromatic diamines are diethyltoluenediamine (a mixture of 1-methyl-3,5-diethyl-2,4-diaminobenzene and 1-methyl-3,5-diethyl-2,6-diaminobenzene), 1,3,5-triethyl2,4-diaminobenzene, 1-ethyl-3,5-diisopropyl, 2,6-diaminobenzene, 1,3,4,6-tetramethyl-2,5-diaminobenzene, 1,4-dimethyl-3,6-diethyl-2,5-diaminobenzene, methylenebis(2,6-diisopropyl-aniline), methylenebis(2,6-diethylaniline), methylenebis(2-methyl-6-ethyl-aniline) and the like. The preferred hindered aromatic diamine is diethyltoluenediamine.

In order to prepare the glycidyl amines of this invention, the hindered aromatic diamine is reacted with an epihalohydrin. Examples of epihalohydrins are epichlorohydrin, epibromohydrin and epiiodohydrin with epichlorohydrin being preferred. In preparing the compositions of this invention, the hindered aromatic diamine is dissolved in an excess of epihalohydrin and the solution is heated at a temperature of 80° C. to the reflux temperature of the epihalohydrin, preferably, 90° C. to 120° C., for a period, generally about 1 to about 16 hours, long enough to complete the addition of the epihalohydrin to the amine. Various catalysts, such as tertiary amines, tertiary amine salts, quaternary ammonium hydroxide, quaternary ammonium salts, alkali metal hydroxides, alkali metal salts and the like, can be used to effect this addition reaction. However, it is preferred to conduct the reaction without a catalyst.

The amount of epihalohydrin used with each mole of aromatic diamine is at least about 8 moles. There is no upper limit to the moles of epihalohydrin that can be used. However, for economic reasons, no more than about 32 moles are used. The preferred molar ratios of epihalohydrin to aromatic diamine are about 12 to 1 to about 24 to 1.

At the completion of the addition reaction, the resulting solution will contain halohydrin amine groups, glycidyl amine groups, glyceryl dihalohydrin and unreacted epihalohydrin. The halohydrin amine groups result from the addition of epihalohydrin to the amine. The glycidyl amine groups and the glyceryl dihalohydrin result from a disproportionation reaction between the halohydrin amine groups and epihalohydrin, hydrogen halide being extracted from the halohydrin amine and added to the epihalohydrin.

The resulting solution which contains halohydrin amine groups and glyceryl dihalohydrin plus the glycidyl amine groups and epihalohydrin is subjected to a dehydrohalogenation with caustic. This dehydrohalogenation can be conducted with sodium hydroxide or potassium hydroxide in flake, pellet or powder form, but preferably, is conducted with aqueous sodium hydroxide, i.e., about 30 to about 70 weight percent sodium hydroxide in water and, preferably, about 40 to about 55 weight percent. The dehydrohalogenation reaction is conducted at a temperature of about 92° to 105° C. for a period of about 1 to 4 hours. Preferably, aqueous caustic is added slowly to the reactor, heated at a temperature sufficient to azeotropically distill epihalohydrin and water. The water is separated from the azeotrope and discarded, and the epihalohydrin is returned to the reactor. The amount of caustic used is substantially equivalent to the equivalents of aromatic amine, i.e., about 4 moles of caustic to each mole of diamine. Excess caustic, about 0 to 15 weight percent excess can be used.

After the dehydrohalogenation reaction is completed, the excess epihalohydrin and the caustic halide are removed, the epihalohydrin by distillation and the caustic halide by filtration or water washing.

In order to obtain a glycidyl amine product which is low in hydrolyzable halide, the glycidyl aromatic amine is subjected to a second dehydrohalogenation step in an inert solvent other than epihalohydrin. Inert solvents that can be used are methylisobutyl ketone, toluene/ethanol mixtures, toluene/isopropanol mixtures, xylene/isopropanol mixtures and the like. The preferred solvent is methyisobutyl ketone. Generally, the second dehydrohalogenation is conducted by dissolving the glycidyl amine in the inert solvent at a solids content of about 40 to about 80%. Caustic, preferably sodium hydroxide in aqueous solution as described hereinbefore, is added in the amount of about 0.2 mole per amine equivalent at a temperature of about 50° C. to 100° C. Heating the two-phase mixture while stirring over a period of about 0.5 to about 2 hours reduces the residual hydrolyzable halide to less than 0.1%. The water phase is discarded and the inert solvent solution is mixed with water and is neutralized. The water phase is removed and residual water is removed by azeotropic distillation. The solution is filtered and the solvent is distilled off. The polyglycidyl amine is recovered at approximately 100% non-volatiles.

Preferred polyglycidyl amines of this invention are polyglycidyl diethyltoluene diamine having an epoxide equivalent weight of 101 to 135 and polyglycidyl methylene bis(2,6-diisopropyl-aniline) having an epoxide equivalent weight of 150 to 200.

The compositions of this invention can be cured with any of the well-known epoxy resin curing agents, e.g., aromatic and aliphatic polyamines, tertiary amines, tertiary amine salts, quaternary ammonium compounds, polybasic acids, polybasic acid anhydrides, Friedel-Crafts catalysts and the like. The preferred curing agents are aromatic and cycloaliphatic polyamines. Cured compositions made from the glycidyl amines of this invention and aromatic polyamines when cured for two hours at 177° C. exhibit moisture conditioned heat distortion temperatures of 230° C. and above.

The glycidyl amine compositions of this invention can be blended with well-known epoxy resins, e.g., diglycidyl ether of Bisphenol A, glycidyl ethers of novolac resins, etc., in order to obtain products which have properties taylored to specific end uses.

The following examples will describe the invention in more detail. Parts and percentages unless otherwise indicated are parts and percentages by weight.

EXAMPLE 1

To a suitable reactor equipped with an agitator, thermometer, and reflux condenser were added 311.1 parts of methylenebis(2,6-diisopropyl-aniline) (MDPA) and 1887 parts of epichlorohydrin. Heat and agitation were applied raising the temperature over a 40 minute period to 109° C. where a slight reflux began. Heating was continued for 7 hours and 45 minutes with the temperature rising to 121° C. under a steady reflux. Heating was discontinued allowing the temperature to drop to room temperature.

The reactor was then equipped with a dropping funnel and an azeotropic distillation apparatus for separating water/epichlorohydrin azeotrope with removal of water and return of epichlorohydrin to the reactor. To the dropping funnel were added 272 parts of 50% aqueous sodium hydroxide. The temperature in the reactor was raised to 92° C. and slow addition of the aqueous sodium hydroxide was begun. A slight vacuum was applied and a water-epichlorohydrin distillation began. The addition of the aqueous caustic was completed in 55 minutes with the temperature being held between 92°–95° C. and with the water being removed from the distillate and the epichlorohydrin being returned to the reactor. The temperature was held at 95° C. for an additional 5 minutes to complete the dehydrohalogenation reaction. Heat was removed allowing the temperature to drop to 80° C. while fitting the reactor for vacuum distillation of the unreacted epichlorohydrin. The temperature was raised to 95° C. where distillation began. Vacuum was applied gradually over 45 minutes with the temperature rising to 100° C. and with full vacuum (30 inches Hg) being applied. After 10 minutes at 100° C., the vacuum was broken and heating was stopped.

Methylisobutyl ketone, 510 parts, was added, followed by 578 parts of water. Heat and agitation were applied for 10 minutes with the temperature at 50°–60° C. The agitation was stopped allowing the brine solution to separate from the organic solution. The brine layer was siphoned off. Water, 510 parts, and 50% aqueous sodium hydroxide, 63.9 parts, were then added. Heat and agitation were applied raising the temperature to 80° C. The temperature was held at 80° C. for 1 hour. Heating and agitation were stopped allowing the aqueous layer to separate from the organic layer. The aqueous layer was siphoned off and 510 parts of water plus about 0.5 part of 30% aqueous sulfuric acid were added. After agitating for 10 minutes, the pH of the aqueous layer was 8.4. Agitation was stopped, and the aqueous layer was siphoned off. Additional water, 510 parts, was added and was agitated at 50°–60° C. for one hour. Heating and agitation were discontinued and the water layer was siphoned off. The reactor was then fitted with a Dean-Stark trap for azeotropic removal of the remaining water. Heat and agitation were applied and at 92° C., distillation began. After 30 minutes heating, the temperature was 100° C. Heating and agitation were discontinued. The reactor contents were cooled slightly and were filtered. The filtered contents were returned to the reactor which was fitted for vacuum distillation. Heat was applied and at 90° C., vacuum was gradually applied with controlled distillation of the methylisobutyl ketone. After 1 hour and 40 minutes, the temperature was 100° C. and full vacuum (30+ inches of Hg) had been applied. After 15 minutes heating, the temperature was 123° C., the vacuum was broken and heating was discontinued.

The resulting product, 470 parts, had a solids content of 96.8% as measured after 30 minutes at 200° C., and epoxide equivalent weight of 178, no measurable hydrolyzable chlorine, and a total chlorine of 1.8%. The physical state of the product was a semi-solid.

One hundred parts of the glycidyl amine and 27.8 parts of methylene dianiline were mixed for 5 minutes at 90°-92° C. The resulting clear solution was de-aired with vacuum and was poured into a mold (⅛ inch thick) preheated to 82° C. The mold was placed in an oven and heated at 82° C. for 1 hour and 15 minutes followed by 1 hour and 45 minutes at 121° C. The resin gelled at the end of this heating period. The gelled resin was then heated for 2 hours at 121° C. and 2 hours at 177° C. The cured transparent air-free casting was cut up into specimens for physical testing. The heat distortion temperature (ASTM D-648 - 264 psi fiber stress load option) on a dry test bar was found to be 218° C. The heat distortion temperature after conditioning at a relative humidity of >95% for 64 hours at 93° C., was found to be 232° C. The % water absorption during this conditioning was 1.76%. The tensile strength of a dry test specimen was 4193 psi, elongation 1.1%, and modulus $0.41 \times 10^6$ psi.

Seventy parts of the glycidyl amine and 63.5 parts of nadic methyl anhydride were heated for 5–8 minutes at 80° C. to form a solution which was then de-aired with vacuum and poured into a mold, preheated to 80° C. After 1 hour and 15 minutes at 93° C. and 10 minutes at 166° C., the resin gelled. The resin was then heated at 166° C. for 4 hours and at 204° C. for 16 hours. The resulting opaque air-free casting was cut up into test specimens. The heat distortion temperature, dry, was 231° C. and, wet, 227° C. The water absorption was 1.99. The tensile strength was 2434 psi, elongation 0.4% and modulus 0.55.

EXAMPLE 2

Following the procedure described in Example 1, 160.2 parts of diethyltoluenediamine and 1998 parts of epichlorohydrin were heated from 117° C. to 128° C. over a period of 6 hours and 57 minutes. To this reaction product were added 288 parts of 50% aqueous sodium hydroxide over a period of one hour and 35 minutes at a temperature of 98° C. while removing water by azeotropic distillation. After the addition of the aqueous sodium hydroxide, the unreacted epichlorohydrin was removed by vacuum distillation at a temperature of 93°-99° C. under full vacuum, 30 in. Hg. Methylisobutyl ketone, 361.8 parts, was added followed by 828 parts of water to dissolve the salt formed from the dehydrohalogenation reaction. The brine was removed and 414 parts of water plus 63 parts of 50% aqueous sodium hydroxide were added. After heating for 1 hour at 80° C., the aqueous layer was removed and 414 parts of water were added. After agitation for 10 minutes, the layers were allowed to separate and the aqueous layer was drawn off. Water, 414 parts, was added. After agitation for 10 minutes at 80° C., 4.5 parts of 30% aqueous sulfuric acid were added to adjust the pH to 7–8. The aqueous layer was drawn off and the remaining water was removed by azeotropic distillation. The reactor contents were then filtered and the filtered solution was heated under vacuum to remove the ketone solvent.

The resulting product, 315.7 parts, had a solids content of 98.07% after ½ hour at 200° C., a Gardner color of 12, a viscosity at 25° C. of 7040 cps (Brookfield No. 6 spindle at 50 RPM), an epoxide equivalent weight of 121.7, and a hydrolyzable chlorine of 0.05%.

One hundred parts of the glycidyl amine were blended with 34.8 parts of isophorone diamine and were poured into a mold to form a ⅛ inch thick casting. The casting was heated for 45 minutes at 93° C. and for 1 hour at 149° C. The heat distortion temperature of the resulting cured casting was 209° C., dry, and 199° C., wet. The water absorption was 2.16%. The tensile strength was 3494 psi, tensile elongation 0.8% and tensile modulus $0.5 \times 10^6$ psi.

EXAMPLE 3

Using the same procedure as described in Example 1, 178.3 parts of diethyltoluenediamine and 1110 parts of epichlorohydrin were reacted followed by dehydrohalogenation with 320 parts of 50% aqueous sodium hydroxide. After the dehydrohalogenation reaction and distillation of the excess epichlorohydrin, 402 parts of methylisobutyl ketone were added followed by 921 parts of water to dissolve the sodium chloride formed in the dehydrohalogenation reaction. The brine was siphoned off and 70 parts of 50% aqueous sodium hydroxide plus 461 parts of water were added for the second dehydrohalogenation reaction. After heating at 82° C. for 1 hour, agitation and heating were discontinued. The aqueous layer was drawn off, 460 parts of water were added, the mixture was agitated for 10 minutes and the aqueous layer was drawn off. The solution was again washed with 460 parts water, the water layer was drained off and the remaining water was removed by azeotropic distillation. After filtering, the ketone solvent was removed by vacuum distillation.

The resulting product, 282 parts, had a solids content of 100%, an epoxide equivalent weight of 127.5, a Gardner color of 12–13, and a Gardner-Holdt viscosity at 25° C. of $Z_5$–$Z_6$. When cured with isophorone diamine using the procedure described in Example 2, comparable results were obtained.

EXAMPLE 4

Using the same procedure described in Example 2, diethyltoluenediamine was reacted with epichlorohydrin to form a polyglycidyl amine having an epoxide equivalent weight of 118, a hydrolyzable chlorine of 0.05% and a total chlorine of 0.67%.

The polyglycidyl diethyltoluene and a number of commercially available epoxy resins were cured with isophorone diamine. The commercially available resins were Araldite MY720, N,N,N',N'-tetraglycidyl methylene dianiline, and Epoxy Resin 0510, the triglycidyl derivative of p-aminophenol and epichlorohydrin. Both of these resins are sold by Ciba-Geigy Corporation. The other commercially available epoxy resins were PGA-X, N,N,N',N'-tetraglycidyl metaxylylene diamine, and PGA-C, N,N,N',N'-tetraglycidyl-1,3-bis(aminomethyl) cyclohexane, both sold by Sherwin-Williams Company, and Epi Rez 509, the diglycidyl ether of Bisphenol A, sold by Celanese Specialty Resins Company. Details of the curing reactions and the physical properties of the cured castings are listed below.

| Epoxy Resin | Epoxide Equivalent | Code |
|---|---|---|
| Polyglycidyl diethyltoluenediamine | 118 | Epoxy A |
| Araldite MY720 | 120 | Epoxy B |
| Epoxy Resin 0510 | 99 | Epoxy C |
| PGA-X | 102 | Epoxy D |
| PGA-C | 104 | Epoxy E |
| Epi Rez 509 | 185 | Epoxy F |

| Epoxy Resin | A | B | C | D | E | F |
|---|---|---|---|---|---|---|
| Parts Resin to Parts Curing Agent | | | | | | |
| Epoxy | | | | | | |
| A | 100 | | | | | |
| B | | 100 | | | | |
| C | | | 100 | | | |
| D | | | | 100 | | |
| E | | | | | 100 | |
| F | | | | | | 100 |
| Isophorone Diamine | 36.0 | 35.4 | 42.5 | 41.7 | 40.9 | 23 |
| Handling Properties | | | | | | |
| Resin Viscosity (cps) | 12,000 | >1,000,000 | 1,300 | 2,800 | 2,500 | 9,000 |
| Mix Viscosity (cps) | 1,050 | 6,100 | 230 | 610 | 400 | 790 |
| Pot Life (Hours) | 4 | 1 | 2 | 3 | 8 | 1 |
| Physical Properties, Cured 1 Hour @ 149° C. | | | | | | |
| Heat Distortion Temp. °C. | | | | | | |
| Dry | 198 | 175 | 161 | 157 | 153 | 139 |
| Wet | 192 | 143 | 128 | 135 | 133 | 124 |
| % H$_2$O Absorption | 1.8 | 2.6 | 3.9 | 2.8 | 2.6 | 2.0 |
| Tensile Strength (psi) | 4,600 | 6,300 | 10,000 | 8,900 | 9,200 | 12,700 |
| Tensile Strain (%) | 1.2 | 1.3 | 2.6 | 1.8 | 2.2 | 5.7 |
| Tensile Modulus (10$^6$ psi) | 0.46 | 0.49 | 0.48 | 0.57 | 0.51 | 0.42 |
| Flexure Strength (psi) | 10,500 | 15,900 | 19,400 | 12,200 | 12,900 | 19,600 |
| Flexure Strain (%) | 2.0 | 3.5 | 4.9 | 2.4 | 2.7 | 7.0 |
| Flexure Modulus (10$^6$ psi) | 0.50 | 0.49 | 0.52 | 0.53 | 0.49 | 0.44 |

EXAMPLE 5

One hundred parts of polyglycidyl methylenebis (2,6-diisopropyl-aniline) (Example 1), epoxide equivalent weight 178, were blended with 27.8 parts of methylene dianiline and the blend was heated at 90°–92° C. for 5 minutes to obtain solution of the components. The solution was de-aired with vacuum and was poured into a mold preheated to 82° C. The resin solution was heated for 1 hour and 15 minutes at 82° C. and 1 hour and 45 minutes at 121° C. to gel the system. The gelled resin was then heated for 2 hours at 121° C. and 2 hours at 177° C. (Casting 5A).

One hundred parts of polyglycidyl diethyltoluene diamine, epoxide equivalent weight 127.5, made using the procedure of Example 2, were blended with 38.8 parts of methylene dianiline. Castings were prepared using the same procedure as described in the first paragraph of this example (Casting 5B).

A casting was prepared from 100 parts of Araldite MY720, epoxide equivalent weight 120, and 41.2 parts of methylene dianiline (Casting 5C). Another casting was prepared from 100 parts of Epoxy Resin 0510, epoxide equivalent weight 99.5, and 49.9 parts of methylene dianiline (Casting 5D). The same procedure described above was used in preparing these castings.

All of the castings, each ⅛ inch thick, were cut into rectangular specimens. The specimens were weighed and their resistance to steam at 149° C. was determined. This steam resistance test was conducted by placing the specimens in a heavy steel container capable of being sealed to retain pressure. The specimens were placed on end in enough water to cover half the specimen. The steel containers were sealed and were heated at 149° C. for determined intervals. The % weight change was determined on each specimen and any change in the appearance of the casting was noted.

| Casting | % Weight Change | | | | | |
|---|---|---|---|---|---|---|
| | 1 Day | 4 Days | 1 Week | 2 Weeks | 3 Weeks | 4 Weeks |
| 5A | +1.4 | +1.6 | +1.6 | +1.6[1] | +1.7 | +1.7 |
| 5B | +3.5 | +4.7[2] | +4.5[1] | +2.8 | +1.8 | +1.0 |
| 5C | +4.6 | +4.9 | +4.8[2] | +3.9 | +3.2 | +2.3 |
| 5D | +5.5 | +5.8[1] | +6.0 | +5.1 | +4.6 | +3.8 |

[1]Opaque
[2]Dulling

EXAMPLE 6

The latency or B-stage stability of the polyglycidyl amines of this invention is demonstrated as follows:

The polyglycidyl amines were mixed with methylene dianiline using just enough heat to form a solution. The resulting solution was poured into an aluminum moisture dish to a depth of ⅛ inch. The dish and resin were placed in a closed container and were left at room temperature. At periodic intervals, Stroke Gels of the solutions were determined by placing a small amount of the solution, sufficient to form a puddle, about 1 cm in diameter, on a cure plate which was set at a temperature of 150° C. A small spatula was pulled through the molten material and the time required to form a gel was recorded.

To 100 parts of polyglycidyl methylenebis(2,6-diisopropyl-aniline), epoxide equivalent weight-174, prepared as described in Example 1, were added and dissolved 28.4 parts of methylene dianiline. The Stroke Gel at 150° C. was determined to be:

| Initial | 49 minutes |
|---|---|
| 1 Day @ R.T. | 45.5 minutes |
| 3 Days @ R.T. | 41 minutes |
| 1 Week @ R.T. | 24 minutes |
| 2 Weeks @ R.T. | 13.75 minutes |
| 3 Weeks @ R.T. | 10.33 minutes |
| 4 Weeks @ R.T. | 6 minutes |
| 6 Weeks @ R.T. | 5.5 minutes |
| 2 Months @ R.T. | 5 minutes |
| 3 Months @ R.T. | 4.25 minutes |
| 4 Months @ R.T. | 3.75 minutes |

To 100 parts of polyglycidyl diethyltoluene diamine, epoxide equivalent weight-121, prepared as described in Example 2, were added and dissolved 40.9 parts of methylene dianiline. The Stroke Gel at 150° C. was determined to be:

| Initial | 14.5 minutes |
| --- | --- |
| 1 Day @ R.T. | 11.5 minutes |
| 3 Days @ R.T. | 7.25 minutes |
| 1 Week @ R.T. | Does not melt |

To 110 parts of Araldite MY720, epoxide equivalent weight-120, were added and dissolved 41.2 parts of methylene dianiline. The Stroke Gel at 150° C. of the blend was determined to be:

| Initial | 3.75 minutes |
| --- | --- |
| 1 Day @ R.T. | 1.67 minutes |
| 3 Days @ R.T. | 10 seconds |
| 6 Days @ R.T. | Does not melt |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. Polyglycidyl amines wherein the amine is a sterically hindered aromatic diamine containing two primary amine groups attached directly to carbon atoms in the aromatic nucleus wherein the carbon atoms are not adjacent to each other, wherein the aromatic diamine is mononuclear or dinuclear, wherein the dinuclear diamine contains one primary amine group attached to each aromatic nucleus and wherein the aromatic nuclei are linked through a methylene bridge, wherein each position ortho to each amine group contains an alkyl substituent having one to three carbon atoms and wherein the polyglycidyl amine contains an epoxide functionality between 3 and 4.

2. The polyglycidyl amine of claim 1 wherein no more than one position ortho to each amine group contains a methyl substituent.

3. The polyglycidyl amine of claim 1 wherein at least 3 of the positions ortho to the amine groups contain $C_2$ or $C_3$ alkyl substituents.

4. The polyglycidyl amine of claim 1 wherein the amine is diethyltoluene diamine.

5. The polyglycidyl amine of claim 1 wherein the amine is methylenebis(2,6-diisopropyl-aniline).

6. Polyglycidyl diethyltoluene diamine having an epoxide equivalent weight of 101 to 135.

7. Polyglycidyl methylenebis(2,6-diisopropyl-aniline) having an epoxide equivalent weight of 150 to 200.

* * * * *